United States Patent
Diaz et al.

(10) Patent No.: US 7,132,640 B2
(45) Date of Patent: Nov. 7, 2006

(54) WAVE INTERROGATED NEAR FIELD ARRAY SYSTEM AND METHOD FOR DETECTION OF SUBWAVELENGTH SCALE ANOMALIES

(75) Inventors: Rodolfo E. Diaz, Phoenix, AZ (US); Michael Watts, Tempe, AZ (US)

(73) Assignee: Arizona Board of Regents, Tempe, AZ (US)

( * ) Notice: Subject to any disclaimer, the term of this patent is extended or adjusted under 35 U.S.C. 154(b) by 0 days.

(21) Appl. No.: 10/505,831

(22) PCT Filed: Mar. 5, 2003

(86) PCT No.: PCT/US03/06920

§ 371 (c)(1),
(2), (4) Date: Sep. 2, 2005

(87) PCT Pub. No.: WO03/081715

PCT Pub. Date: Oct. 2, 2003

(65) Prior Publication Data

US 2006/0065856 A1 Mar. 30, 2006

Related U.S. Application Data

(60) Provisional application No. 60/361,650, filed on Mar. 5, 2002.

(51) Int. Cl.
*H01J 3/14* (2006.01)

(52) U.S. Cl. .................... 250/216; 250/306; 343/721

(58) Field of Classification Search ................ 250/216, 250/234, 306–308; 343/721, 795, 807
See application file for complete search history.

(56) References Cited

U.S. PATENT DOCUMENTS

| 5,166,697 A | 11/1992 | Viladevall et al. ........... 343/727 |
| 5,696,372 A | 12/1997 | Grober et al. ............... 250/216 |
| 6,288,856 B1 | 9/2001 | Ottesen et al. ................ 360/31 |
| 7,019,704 B1 * | 3/2006 | Weiss .......................... 343/770 |

OTHER PUBLICATIONS

Igasaki, et al., "High efficiency electrically-addressable phase-only spatial light modulator", Optical Review, vol. 6, No. 4 (1999) pp. 339-344.
Edwards et al., "Investigation of photoconductive silicon as a reconfigurable antenna", SPIE vol. 1918, Smart Sensing, Processing, and Instrumentation, (1993) pp. 344-353.

* cited by examiner

*Primary Examiner*—Kevin Pyo
(74) *Attorney, Agent, or Firm*—McDonnell Boehnen Hulbert & Berghoff LLP

(57) ABSTRACT

An array of antenna elements (20) can be used to detect subwavelength sized anomalies on a surface below the array. An array (20) is illuminated at optical frequencies by a coherent optical energy source (26). The change in reactance and radiated power of the antenna elements that results from the proximity of the anomaly to the near field of the antenna element's open-circuited is detected and holographically filtered to eliminate the radiation caused by the antenna array itself. Image processing is performed on the detected scattered radiation (100) to determine whether an anomaly is present and to locate the anomaly and its characteristics.

44 Claims, 9 Drawing Sheets

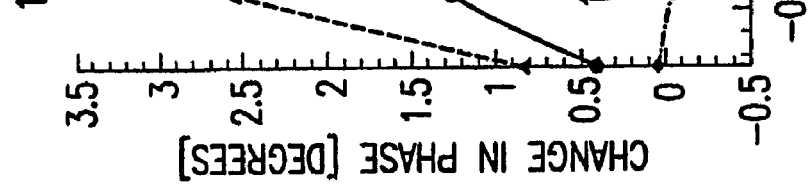

WAVE INTERROGATED NEAR FIELD ARRAY SYSTEM AND METHOD FOR DETECTION OF SUBWAVELENGTH SCALE ANOMALIES

CROSS REFERENCE TO RELATED APPLICATION

This application claims priority to provisional application Ser. No. 60/361,650 filed 05 Mar. 2002 entitled: "A HIGH SENSITIVITY ANTENNA ELEMENT FOR NEAR FIELD PROBE APPLICATIONS", which is incorporated herein by reference in its entirety.

BACKGROUND OF THE INVENTION

1. Field of the Invention

In one aspect, this invention is a method and system for detecting sub-wavelength size anomalies in a substrate using optical radiation and an array of resonant photonic open feed antenna elements. In another aspect, this invention is directed to a closed flux resonant antenna that may be used in a system for detecting sub-wavelength size anomalies in a substrate.

2. Background Information

On semiconductor substrates, anomalies, such as process contaminants, post-polishing substrate fragments, or voids need to be accurately located and identified in order to obtain the cleanliness required for the next generation of integrated microcircuits. Because of technological advances, the critical anomaly size is currently less than 80 nm. Because of their minute size, such anomalies are beyond the detectability limit of conventional optical beam scattering approaches, which is determined by the diffraction limit: i.e. approximately one third of a wavelength. In the optical range, this is of the order of 150 to 200 nm since the wavelength of light is on the order of 400 to 600 nm. To extract shape information, the object size should be closer to one wavelength. With standard optical scattering approaches, the smallest objects that can be reliably examined thus are approximately 500 nm, significantly larger then the current critical anomaly size of 80 nm. Because optical instruments and sources in the visible range are very mature and reliable, an optical system that circumvents the diffraction limit would be a much more attractive alternative to perform this function than developing new instruments and sources operating at frequencies above the optical range. This is because mature scatterometry systems which operate at higher frequencies and are capable of scanning productions sized wafers do not yet exist.

Investigators have proposed schemes to defeat the diffraction limit by concentrating the radiated energy into subwavelength areas. An early scheme using a tapered fiber probe succeeded in concentrating the illumination to an area approximately one tenth of a wavelength in diameter. This came, however, at the expense of a tremendous degradation in illumination, as a transmission efficiency of $10^{-5}$ was reported. Another scheme to defeat the diffraction limit by interposing an open feed bow-tie resonant antenna element in the path of the illuminating wave is described in U.S. Pat. No. 5,696,372, which is incorporated by reference herein in its entirety. This approach resulted in superior transfer of power from an incident wave to an observation region than previous techniques. The open circuited bow-tie antenna effectively blocks a radiated wave and concentrates its energy in the open circuited gap region of the antenna. The result is an illuminated area of the order of one sixth to one tenth of a wavelength across, with a transmission efficiency ranging from 0.5% to as high as 30%.

The techniques used in the prior art generally suffer from very small transmission efficiencies (i.e., the ratio of incident power to power at the tip) because the concentration of the wave energy is achieved by guiding the wave through closed waveguides that are well below cutoff. That is, the waveguide dimensions are so small compared to the wavelength that most of the incident energy is reflected before reaching the observation aperture at the tip. Further, when used with wavelengths in the optical range rather Man in the microwave range, an inductive load connected to the gap in the bow-tie configuration can change the transmission efficiency from 0.5% to nearly 100%. Thus, the proximity of the object to be detected can dramatically alter the transmission efficiency of the probe by changing the reactance in the near field. A second issue left unaddressed, but which is critical to the application of defect detection on large semiconductor wafers, is that the minuteness of the spot-size implies an enormous scanning time as the illuminated region is physically moved over the area to be examined.

Accordingly, a system and method for rapidly scanning large wafer areas to locate and identify defects or debris addressing the drawbacks of the prior art is needed.

SUMMARY OF THE INVENTION

The present invention exploits the benefits of near-field energy concentration, while retaining the convenience and speed of far-field scattering data collection.

One exemplary embodiment of the present invention is a Wave Interrogated Near-Field Array System comprising an array of resonant open feed antennas arranged in a plane substantially parallel to the surface of a target substrate under investigation. An incident coherent light energy beam is directed toward the substrate. Radiation scattered by any anomaly in the substrate is re-radiated by the array. The re-radiated energy corresponding to the anomaly is filtered using a holographic filter corresponding to the scattered radiation caused by the antenna array in the absence of any anomaly. The filtered radiation is used to detect any anomaly.

In one embodiment, open feed bow-tie antennas may be used in the Wave Interrogated Near-Field Array System. The resonant amplification of the incident energy field at the tip of the elements exceeds the field strength of the incident wave. The elements are not interrogated one by one but rather the response of the entire array is detected at the same time through holographic filtering of the array's scattering signature.

In another exemplary embodiment of the present invention, a closed-flux-path antenna element is used in the Wave Interrogated Near Field Array system. This element is optimized to obtain a maximum power concentration near its feed-point, while at the same time minimizing the spot size illuminated. Since the antenna element is a closed-flux-path element, its near field is less sensitive to perturbations caused by a nearby surface, such as the surface being inspected, yet retains its sensitivity to sub-wavelength perturbations of the surface being inspected. The antenna element includes a dielectric substrate; an outer conducting strip having a width of approximately $\lambda/24$ formed in a rectangular configuration supported by the dielectric substrate, wherein the overall length of the rectangular shape is approximately $\lambda/2.8$ and the overall width of the rectangular shape is approximately $\lambda/4.8$; a first conducting strip extending from the outer conducting strip toward the interior of the rectangular configuration parallel to the portions of the outer conducting strip forming the length thereof and equidistant from the portions, the first conducting strip terminating in a first end; and a second conducting strip extending parallel to the portions of the outer conducting strip forming the length thereof and equidistant from the portions, the second conducting strip extending from a point on the outer conducting strip opposite the first conducting strip toward the interior of the rectangular configuration and terminating in a second end; whereby the first and second ends are separated by a distance of approximately $\lambda/16$.

BRIEF DESCRIPTION OF THE DRAWINGS

FIGS. 16 and 17 are charts illustrating the different amplitude and phase radiation profiles respectively produced by the antenna element shown in FIGS. 8–10 when in the presence of different types of anomalies.

DETAILED DESCRIPTION OF THE PRESENT INVENTION

Figure 1:
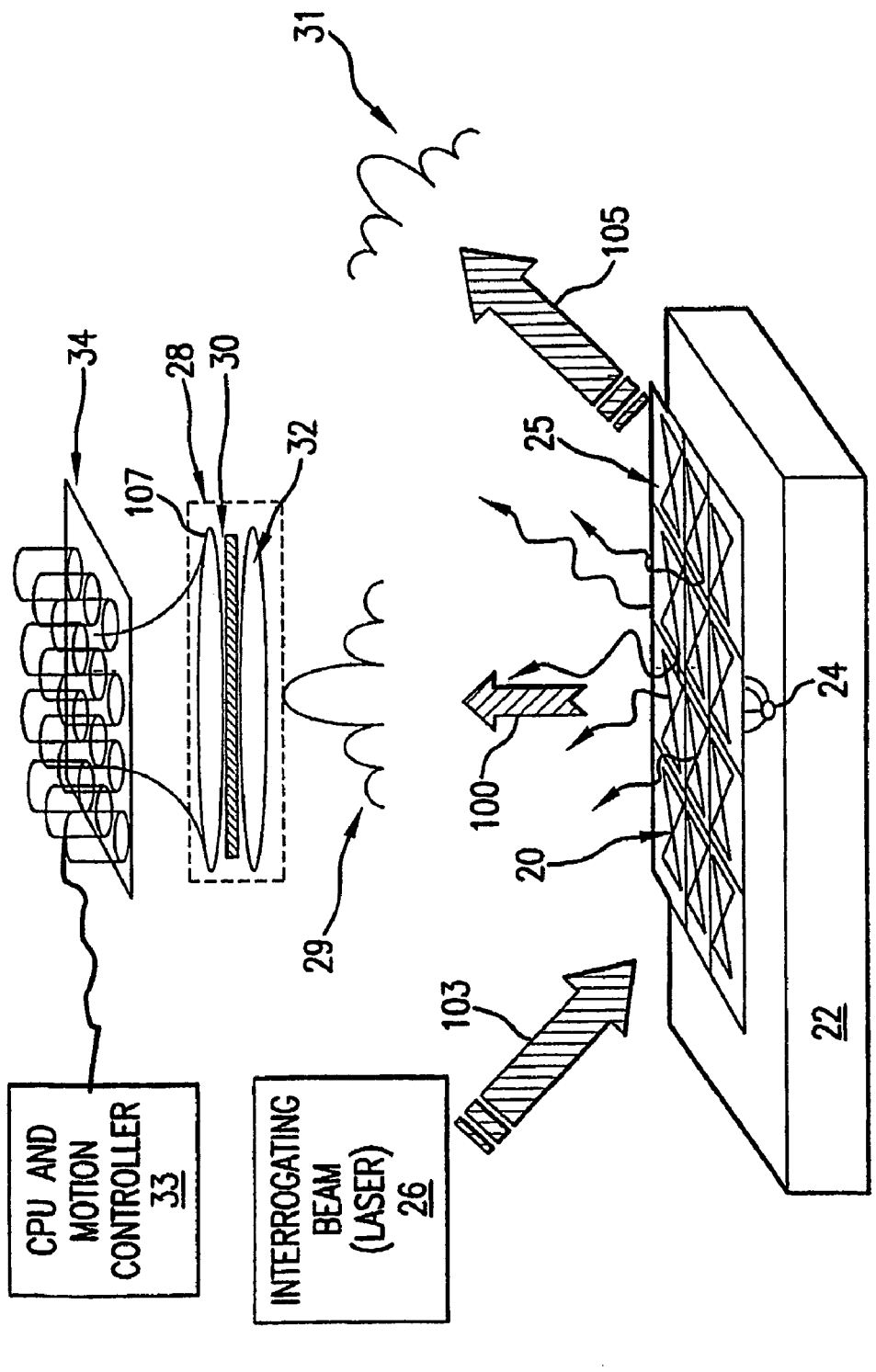
FIG. 1 is a diagrammatic view of a first exemplary embodiment in accordance with the present invention.
Figure 2:
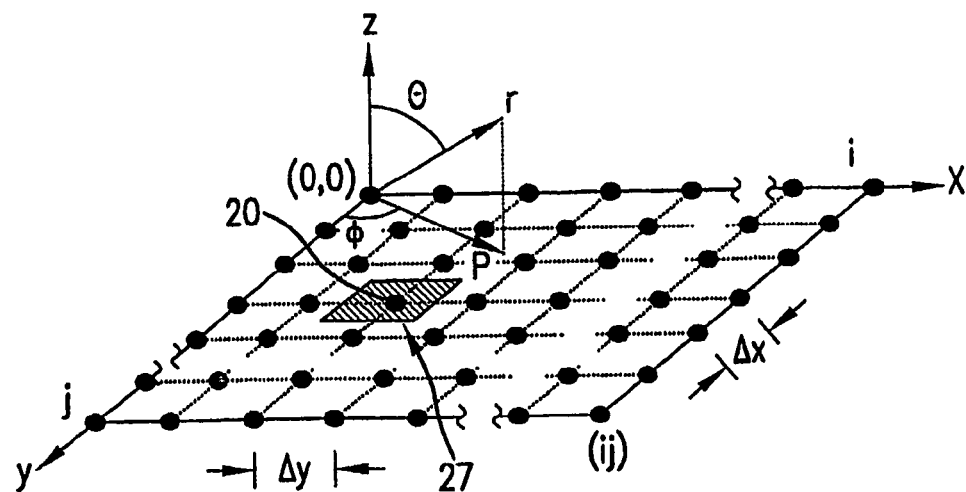
FIG. 2 is a diagrammatic view showing an array of antenna elements for use in one embodiment of the present invention.
Figure 3:
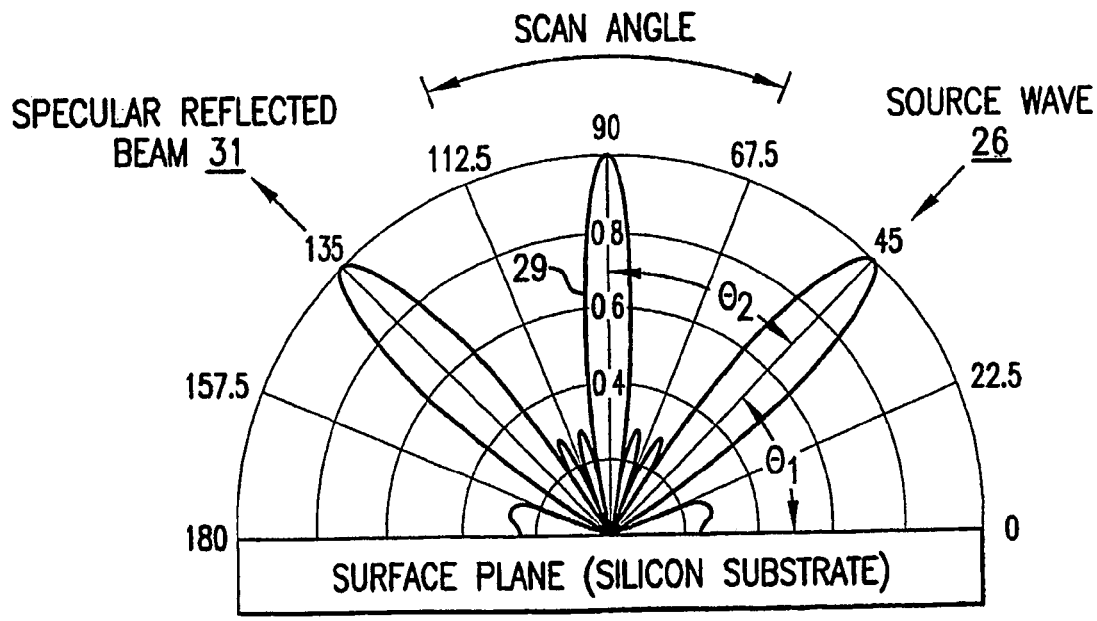
FIG. 3 is a diagrammatic view showing scattered energy from an array and substrate illuminated by a reference source in one embodiment of the present invention.

FIGS. 1–3 depict one exemplary embodiment of the present invention. A wave interrogated near field array system 18 is shown to include a plurality of antenna elements or probes 20, which may be constructed of open circuited bow-tie antennas on an optically transparent substrate 25. The transparent substrate 25 may be fabricated from $SiO_2$, BK7, or other suitable optical glass. A substrate 22 to be examined for anomalies may be provided under the array of antenna elements 20. The substrate 22 may for instance be silicon, metallic, or magnetic media. The array typically is placed at a height of approximately 70 nm from the surface of the substrate 22 to be examined. The antenna elements 20 may be illuminated by a reference source 26, which may be coherent monochromatic source, for example a laser, emitting electromagnetic energy having a characteristic wavelength ($\lambda$), producing a free space wave. In one exemplary embodiment, the characteristic wavelength $\lambda$ of the energy source is between 400 and 830 nm, although the present invention is not limited to that range and could be applied to systems where the characteristic wavelength $\lambda$ of the energy source is between approximately 260 nm and approximately 830 nm.

The arrangement of the antenna elements 22 into an array, as shown in FIG. 2, means that the antenna array behaves like an optical grating. In one exemplary embodiment, the antenna elements are spaced equally from each other, separated by a center-to-center distance of $\sqrt{2}$ times $\lambda$, or approximately $1.41\lambda$, where $\lambda$ is the previously mentioned characteristic wavelength of the energy source to be utilized. Accordingly, when the reference source 26 emits energy 103 toward the array over the substrate 22, scattered energy 100 with a scattering signature of the array and substrate 29 and a forward scattered energy 105 with a scattering signature of specular reflection 31 result. As shown in FIG. 3, the light source directs its energy at an incident angle $\theta_1$ toward the substrate under investigation. In one exemplary embodiment, incident angle $\theta_1$ is 45 degrees. In this embodiment, a first order of scattered radiation consisting of forward scattered energy 105 reflects off of the substrate at an angle of 135 degrees. A second order of scattered energy 100 is scattered at an angle $\theta_2$ away from the energy source. In the exemplary embodiment, $\theta_2$ is 45 degrees, so the scattering signature 29 of scattered energy 105 is present directly above the substrate (i.e. 90 degrees from the surface of the substrate) as shown in FIG. 3. A detection apparatus, as discussed in detail below, would then scan an angle of $\pm 22.5$ degrees from the center of the scattered energy signature 29, to collect all of the information in the second order of scattered radiation.

As shown in FIG. 2, the substrate 22 to be examined may be scanned in at least one spatial dimension under the array of antenna elements 20. Each antenna element 20 of the array has a corresponding unit cell 27, designating the physical area in which the near field of that antenna element predominates. Scanning may be achieved by physically moving the substrate 22 or the array of antenna elements 20 the length or width of one unit cell 27 or portion or multiple thereof relative to the array of antenna elements 20 or the substrate 22, respectively.

Returning now to FIG. 1, a system of Fourier optics 28 maybe used to collect and filter scattering radiation 100 from the substrate 22 and array of antenna elements 20. The system 28 may be placed in such a manner to avoid collecting the specular reflection 105 of the incident radiation from the reference source 26, and instead primarily collect the scattering signature 29 of the energy 100 scattered from the array of antenna elements 20 and the substrate 22. The system of Fourier optics 28 may contain a lens 32 and holographic filter 30. The filter 30 may be photographically created from a Fourier transform of an array of unperturbed elements 20. In other words, the holographic filter 30 may correspond to the energy scattered by an array of antenna elements 20 when no anomaly is present in the substrate 22 under investigation The holographic filter 30 may be amplitude negative to filter radiation from a baseline, unperturbed (i.e. no anomalies present) array, blocking that scattered radiation from passing to detector 34. The lens 32 may perform an inverse Fourier transform function so that the system 28 transforms amplitude and phase distortions from particular elements of the array of antenna elements 20 into a visible image. In one exemplary embodiment, lens 32 is placed so that its front focal point is on the array of antenna elements 20.

Detector 34, which may be an array of fiber optics (including an associated optical detector such as a photodiode), a charge coupled device (CCD), or other optical detection apparatus may be placed near a rear focal point of the lens 32 or focusing lens 107, and may detect the energy scatted by any anomalous element or elements, as a function of scanning position. A computer 33, having suitable software or firmware, may be used to deduce the size, shape, position, and composition of the anomalies 24 under the array of antenna elements 20 and display this information to a user. This may be accomplished by comparing the results with a computed or empirical database, as discussed in further detail herein with reference to FIGS. 16–17.

Figure 4:
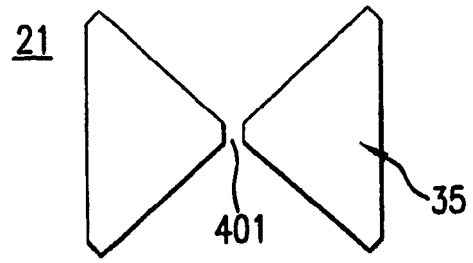
FIG. 4 is a top view of an exemplary antenna element for use in the embodiment of FIG. 1.

FIG. 4 depicts a bow-tie antenna element 21 which may be used as an antenna element 20 in the Wave Interrogated Near Field Array system 18. The conductive arms 35 of the bow-tie may be fabricated from metal, such as chromium or aluminum. A change in reactance and radiated power of the antenna element 20 results from the proximity of an anomaly 24 to the near field of the antenna element's open-circuited region. Since a change in reactance of the antenna element 20 results in a change of the surface currents that flow on the antenna element, a change in the amplitude and phase of the energy scattered by that antenna element occurs. Further details of an exemplary bow-tie antenna element suitable for use in this exemplary embodiment of the present invention are set forth in U.S. Pat. No. 5,696,372, previously incorporated by reference herein.

In fabricating the holographic filter 32 for use in the system shown in FIG. 1, the film emulsion and exposure time may be controlled such that all maxima in the pattern fully expose the film, and all minima and their immediate neighborhood remain undeveloped. This results in a mask that blocks out the maxima of the pattern from the unperturbed array and thus results in the minimum transmission of that signal. Other methods of implementing holographic filters are well known to one skilled in the art of optical pattern recognition. For instance there are methods for generating phase-only holographic filters in real time based on an input computer file by digitally controlling a transparent liquid crystal display, that are well known to one of ordinary skill in the art, such as the methods described in Igasaki, et al., "High efficiency electrically-addressable phase-only spatial light modulator", Optical Review, vol. 6, no. 4 (1999) p. 339–344, which is incorporated herein by reference. Alternatively, the holographic filter may be performed entirely in a programmable digital computer using well-known digital imaging processing techniques.

In an alternate embodiment of the present invention, the baseline unperturbed image (i.e. the radiation signature of the antenna array when an anomaly is not present) is created in real time by combining the scattering from two arrays, one on the detection system and the other an ideal unperturbed array, in the same optical imaging system in such away that the image from the unperturbed array is delayed by 180 degrees and then coherently added to the image from the array on the detection system. This field distribution is then Fourier transformed again to yield an image. The intensity of this subtracted image will be low if the array on the detection system is unperturbed, however, if one element is perturbed, the area corresponding to that element appears much brighter.

Because of the properties of the Fourier transform, the scattering pattern (and therefore the hologram) of a regular periodic array of a large number of identical objects is uniquely correlated to the scattering properties of a single object. As a result, if the scattering from one of the objects in an array is perturbed, that object can be singled out in real time by filtering the Fourier transform of the perturbed array through the hologram of the unperturbed array. At the detector 34, the perturbed element will appear as the only illuminated spot (about half a wavelength across) in the field of view.

Figure 5:
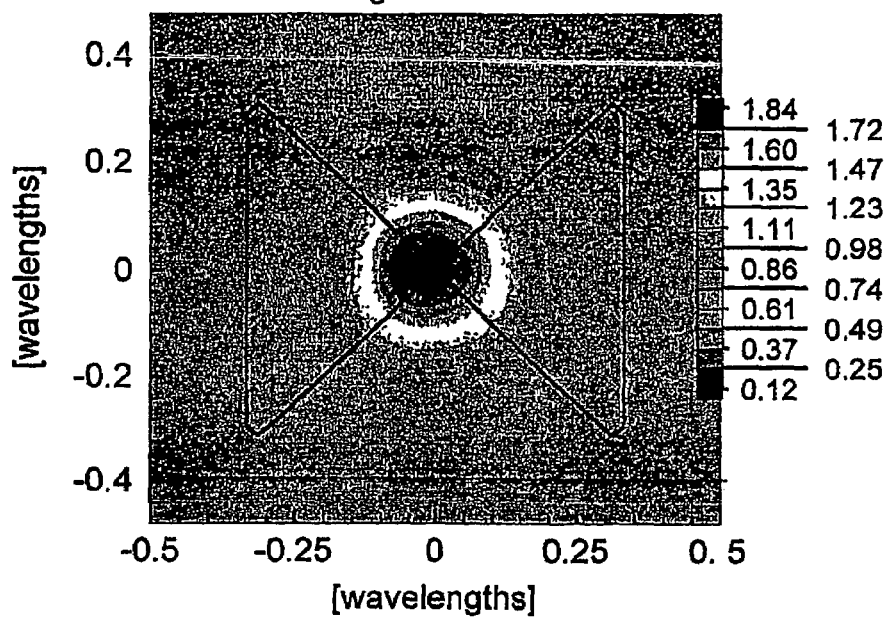
FIG. 5 is a top view showing the electric field radiated by a bow-tie antenna element, which may be used in one embodiment of the present invention, in free space when illuminated by a reference source.
Figure 6:
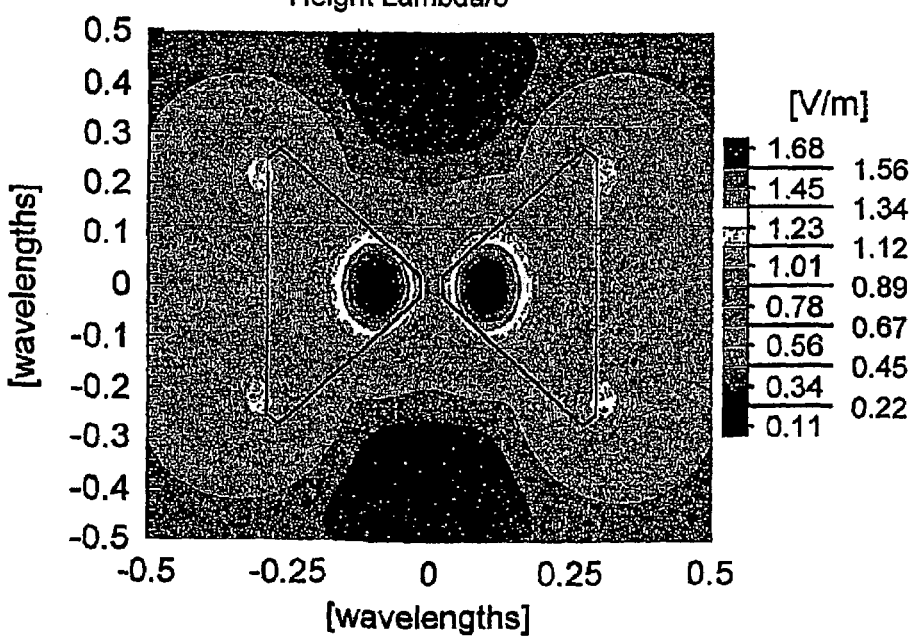
FIG. 6 is a top view showing the electric field radiated by a bow-tie antenna element, which may be used in one embodiment of the present invention, near a substrate when illuminated by a reference source.
Figure 7:
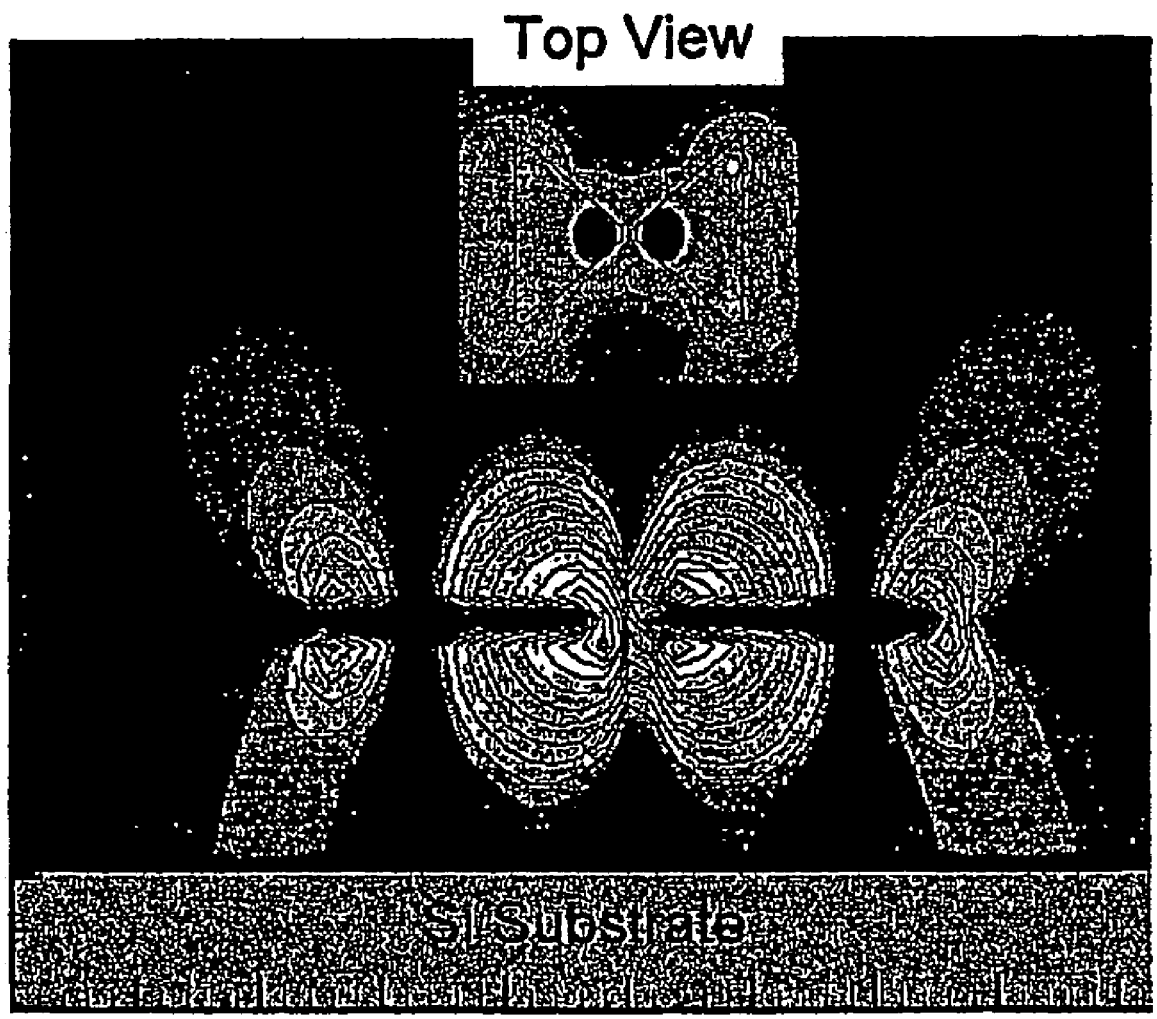
FIG. 7 is a side view showing the magnitude of the normal electric field flux radiated by a bow-tie antenna element near a substrate when illuminated by a reference source.

FIGS. 5 through 7 illustrate a bow-tie antenna element which is of the order of one half wavelength ($\lambda/2$) in length of the characteristic wavelength of the energy source 26, shown in FIG. 1. As shown in FIG. 5, when the bow-tie is in free space, with no large surfaces nearby, it concentrates the incident energy into a spot having a diameter of approximately one eighth of the wavelength at its feed point. As FIG. 6 shows however, when the bow-tie is near a large dielectric surface (such as Silicon) to perform an inspection, its focusing region splits into two spots near the feed and two larger regions at the ends of the bow-tie. This distribution of energy, seen in greater detail in the side view of FIG. 7, introduces some ambiguity in the location of any measurement performed.

Figure 8:
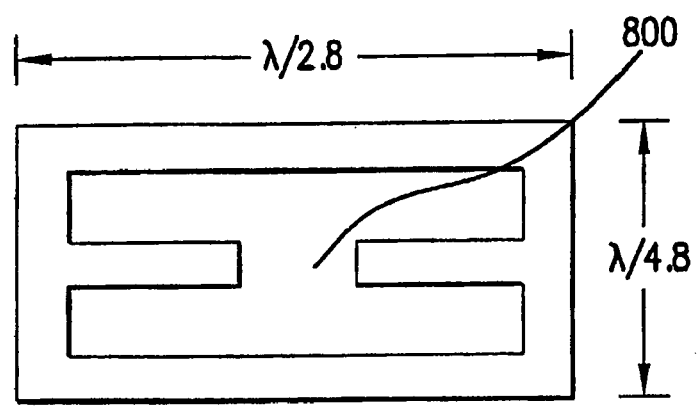
FIG. 8 is a top view of an antenna element which is used in one embodiment of the present invention.
Figure 9:
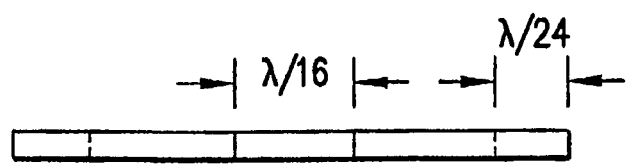
FIGS. 9 and 10 are side views of the antenna element shown in FIG. 8.
Figure 10:
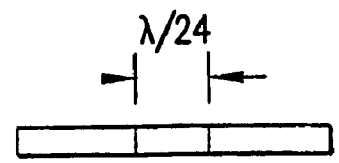
Figure 11:
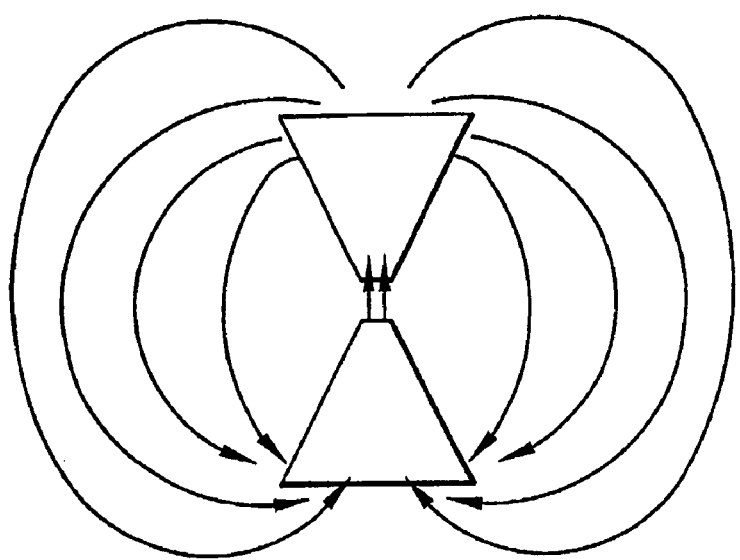
FIG. 11 is a diagrammatic view illustrating the current flux paths in one antenna element for use in one embodiment of the present invention.

FIGS. 8–10 show a closed flux-path open feed antenna element used in another exemplary embodiment of the present invention, along with the typical dimensions of the new antenna element This antenna element configuration obtains a maximum power concentration near its feed-point 800, while at the same time minimizing the spot size illuminated. Since the element is closed-flux-path element, its near field is less sensitive to perturbations caused by a nearby surface, such as the substrate 22 being inspected as shown in FIG. 1, yet retains its sensitivity to sub-wavelength perturbations of the surface being inspected.

Figure 12:
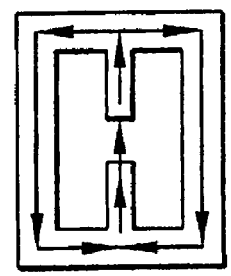
FIG. 12 is a diagrammatic view illustrating the current flux paths in one antenna element for use in one embodiment of the present invention.
Figure 13:
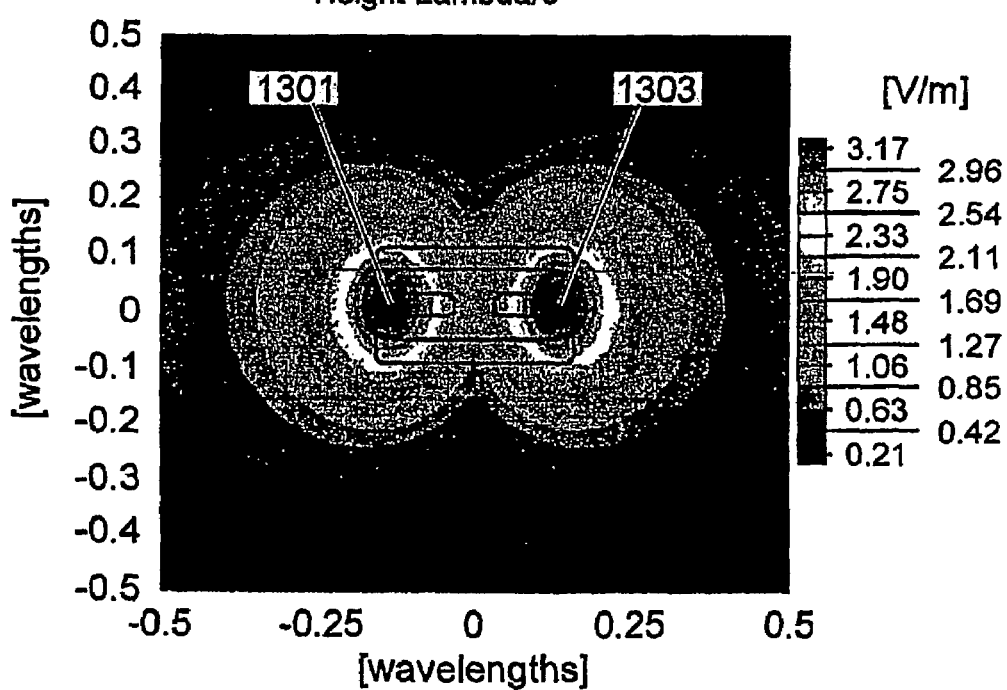
FIG. 13 is a top view showing the electric field radiated by the antenna element shown in FIGS. 8–10, which may be used in one embodiment of the present invention, near a substrate when illuminated by a reference source.
Figure 14:
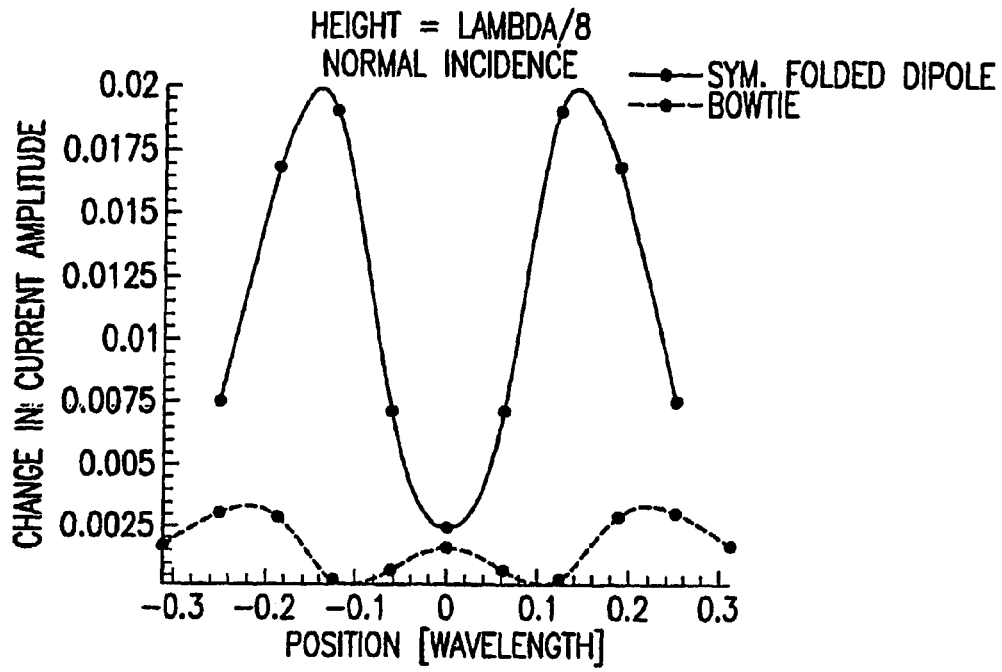
FIG. 14 is a chart illustrating the difference in amplitude sensitivity between the antenna element shown in FIG. 4 and the antenna element shown in FIGS. 8–10 when used in a system in accordance with the present invention.
Figure 15:
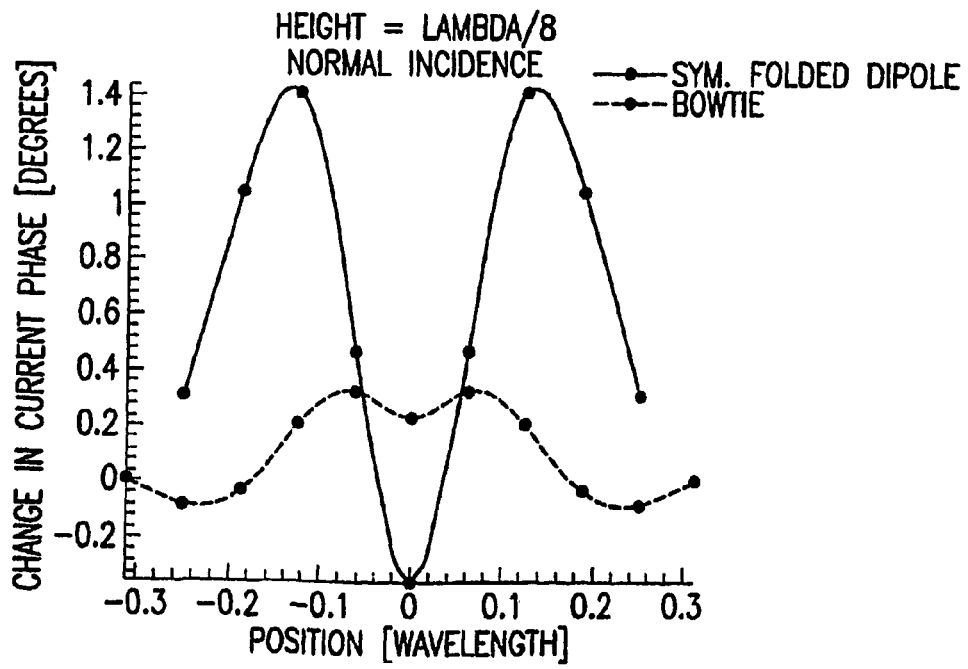
FIG. 15 is a chart illustrating the difference in phase sensitivity between the antenna element shown in FIG. 4 and the antenna element shown in FIGS. 8–10 when used in a system in accordance with the present invention.

FIGS. 11–15 illustrate advantages of using a folded dipole closed flux-path element over a bow-tie element to detect anomalies in a substrate. As FIG. 12 illustrates, the insensitivity to perturbation by surfaces near of the folded dipole antenna element is due to the complete confinement of its total current (displacement plus conduction) within the body of the element itself. FIG. 13 shows the concentration of energy just under the closed flux folded dipole antenna element when that element is near a substrate, such as substrate 22 shown in FIG. 1. The energy is concentrated in two well-defined spots 1301 and 1303 and its intensity (the square of the electric field) is approximately 3.5 times greater than in the case of the bow-tie antenna configuration shown in FIG. 6. FIG. 14 illustrates the increased sensitivity of a closed flux folded dipole antenna element in accordance with the present invention compared to the bow-tie antenna element. When the respective antenna elements are suspended approximately 80 nm above a silicon surface, a 40 nm plastic defect in the surface causes approximately a 2% change in the current amplitude of the closed flux folded dipole element as opposed to an approximate 0.35% change for a bow-tie element. Similar gains are seen in the phase perturbation of the element as shown in FIG. 15. For holographic filtering, a 1% amplitude change and 1° of phase difference are typically adequate for detection of an anomaly in a substrate.

FIGS. 16 and 17 illustrate scattered energy re-radiated by a folded dipole antenna element suspended above three different types of anomalies. Lines 1601 and 1701 show the change in amplitude and phase, respectively, of scattered energy when a folded dipole antenna element is suspended 70 nm above an anomaly comprising a 30 nm silicon cube on the surface of the substrate under investigation. Lines 1603 and 1703 show the change in amplitude and phase, respectively, of scattered energy when a folded dipole antenna element is suspended 70 nm above an anomaly comprising a 30 nm metal cube on the surface of the substrate under investigation. Finally, lines 1605 and 1705 show the change in amplitude and phase, respectively, of scattered energy when a folded dipole antenna element is suspended 70 nm above an anomaly comprising a 30 nm void in the surface of the substrate under investigation.

The manufacturability of antenna elements in the bow-tie and closed flux folded dipole configuration as illustrated will be apparent to one of ordinary skill in the art. At optical wavelengths, these antenna elements require the fabrication of sub-micron scale structures with details in the tens-of-nanometers range. As such, electron-beam lithography (EBL) is the technique of choice for fabricating these structures. In addition, micromachining and micropatterning approaches exist that are capable of creating the desired antenna structures, with a distance between outer edges of conductive arms of a bow-tie of approximately 300 nm and a gap between the arms of approximately 50 nm. Also, virtual antennas in situ may be created on the surface of a photoconductive substrate, as is well known to one of skill in the art as demonstrated by Edwards and Nunnally, SPIE 1918, Smart Sensing, Processing, and Instrumentation, 1993, pp. 344–353, which is incorporated by reference herein. As mentioned, the bow-tie or closed flux folded dipole antenna elements may be constructed of chromium or aluminum.

The scanning procedures used with atomic force microscopy may be used to obtain the subwavelength mechanical scanning. Likewise the separation between the array and the surface of the substrate under investigation may be controlled by present day magnetic media recording approaches that are known to enable reliable head-to-disk clearance in the 40 nm to 100 nm range as shown in U.S. Pat. No. 6,288,856, which is incorporated herein by reference in its entirety.

Although the present invention has been described in detail with reference to exemplary embodiments thereof, it should be understood that various changes, substitutions and alterations can be made hereto without departing from the scope or spirit of the invention, which is defined by the appended claims. For example, holographic filters may be created digitally and thus the detector may directly receive the scatted radiation energy from the antenna array and substrate.

We claim:

1. A method for detecting at least one anomaly on a target substrate having a substantially planar surface, comprising:
  a) providing an array of resonant photonic open-feed antenna elements spaced apart from one another and arranged in a plane substantially parallel to the surface of the target substrate;
  b) directing an incident energy beam of coherent light from an energy source toward the target substrate, the energy beam having an characteristic wavelength ($\lambda$), so that the energy beam is scattered by the anomaly and the array of antenna elements;
  c) re-radiating, by at least one of the antenna elements, energy scattered by the at least one anomaly on the target substrate;
  d) providing a holographic filter corresponding to energy scattered by the array of antenna elements when no anomaly is present on the target substrate;
  e) filtering the scattered and re-radiated energy using at least the holographic filter to produce a filtered result corresponding to the energy scattered by the at least one anomaly; and
  f) determining from the filtered result whether the at least one anomaly is present on the substrate.

2. The method of claim 1, wherein the array of resonant photonic open-feed antenna elements are supported on an optically transparent substrate.

3. The method of claim 2, wherein the optically transparent substrate is formed from material selected from the group consisting of $SiO_2$, BK7 and optical glass.

4. The method of claim 1, wherein the energy source is a laser having a characteristic wavelength between about 830 nm and about 400 nm.

5. The method of claim 1, wherein the open-feed antenna elements are bow-tie antenna elements.

6. The method of claim 1, wherein the open-feed antenna elements are closed flux path folded dipole antenna elements.

7. The method of claim 1, wherein the incident energy beam is directed toward the target substrate at an angle of $\theta$ degrees measured from the surface of the target substrate, such that at least two predominant orders of scattered radiation are created, comprising a forward scattered radiation order at an angle of $180-\theta$ degrees measured from the surface of the target substrate containing the specular reflection of the incident energy beam, and a diffracted radiation order, containing scattered and re-radiated radiation from the target substrate and array of antenna elements.

8. The method of claim 7, wherein the filtering step e) operates only the diffracted radiation order and not the forward scattered radiation order.

9. The method of claim 8, wherein $\theta$ is 45 degrees.

10. The method of claim 1, wherein the holographic filter is an algorithm performed in a programmable digital processor and wherein the filtering step e) comprises:
  converting the scattered and re-radiated energy into digital data; and
  filtering the digital data using at least the holographic filter to produce a filtered result corresponding to the energy scatted by the at least one anomaly.

11. The method of claim 10, wherein the converting the scattered and re-radiated energy step is performed using a charge coupled device.

12. The method of claim 10, wherein the converting the scattered and re-radiated energy step is performed using a fiber optic array and associated optical receiver.

13. The method of claim 1, wherein the holographic filter is a physical holographic filter, further comprising:
  g) converting, before step f), the filtered result to digital data.

14. The method of claim 13, wherein the determining step f) is performed in a programmable digital processor utilizing the digital data generated in step g).

15. The method of claim 1, further comprising:
  g) determining from the filtered result the location of the at least one anomaly on the target substrate.

16. The method of claim 1, further comprising:
g) determining from the filtered result whether the at least one anomaly is a void or a particle.

17. The method of claim 1, further comprising:
g) determining from the filtered result whether the at least one anomaly is formed of metallic or non-metallic material.

18. A system for detecting at least one anomaly on a target substrate having a substantially planar surface, comprising:
an array of resonant photonic open-feed antenna elements spaced apart from one another and arranged in a plane substantially parallel to the surface of the target substrate;
an energy source for directing an incident energy beam of coherent light toward the target substrate, the energy beam having an characteristic wavelength ($\lambda$), the energy beam being scattered by the anomaly and the array of antenna elements;
a filter, comprising a holographic filter corresponding to energy scattered by the array of antenna elements when no anomaly is present on the target substrate for filtering the scattered and re-radiated energy to produce a filtered result corresponding to the energy scattered by the at least one anomaly;
an optical detector, for receiving the filtered result and converting the filtered result to digital data; and
a processor, for processing the digital data and determining from the digital data whether the at least one anomaly is present on the substrate.

19. The system of claim 18, wherein the array of resonant photonic open-feed antenna elements are supported on an optically transparent substrate.

20. The system of claim 19, wherein the optically transparent substrate is formed from material selected from the group consisting of $SiO_2$, BK7 and optical glass.

21. The system of claim 18, wherein the energy source is a laser having a characteristic wavelength between about 830 nm and about 400 nm.

22. The system of claim 18, wherein the open-feed antenna elements are bow-tie antenna elements.

23. The system of claim 18, wherein the open-feed antenna elements are closed flux path folded dipole antenna elements.

24. The system of claim 18, wherein the incident energy beam is directed toward the target substrate at an angle of $\theta$ degrees measured from the surface of the target substrate, such that at least two predominant orders of scattered radiation are created, comprising a forward scattered radiation order at an angle of 180-$\theta$ degrees measured from the surface of the target substrate containing the specular reflection of the incident energy beam, and a diffracted radiation order, containing scattered and re-radiated radiation from the target substrate and array of antenna elements.

25. The system of claim 24, wherein the filter is positioned to receive and filter only the diffracted radiation order and not the forward scattered radiation order.

26. The system of claim 25, wherein $\theta$ is 45 degrees.

27. The system of claim 18, wherein the optical detector is a charge coupled device.

28. The system of claim 18, wherein the optical detector is a fiber optic array and associated optical receiver.

29. The system of claim 18, wherein the processor has further functionality for determining from the digital data the location of the anomaly on the target substrate.

30. The system of claim 18, wherein the processor has further functionality for determining from the digital data whether the anomaly on the target substrate is a void or a particle.

31. The system of claim 18, wherein the processor has further functionality for determining from the digital data whether the anomaly on the target substrate is formed of metallic or non-metallic material.

32. A system for detecting at least one anomaly on a target substrate having a substantially planar surface, comprising:
an array of resonant photonic open-feed antenna elements spaced apart from one another and arranged in a plane substantially parallel to the surface of the target substrate;
an energy source for directing an incident energy beam of coherent light toward the target substrate, the energy beam having an characteristic wavelength ($\lambda$), the energy beam being scattered by the anomaly and the array of antenna elements;
an optical detector, for receiving the scattered and re-radiated energy and converting the energy to digital data; and
a digital holographic filter corresponding to energy scattered by the array of antenna elements when no anomaly is present on the target substrate, for digitally filtering the digital data corresponding to the scattered and re-radiated energy to produce filtered digital data corresponding to the energy scattered by the at least one anomaly; and
a processor, for processing the filtered digital data and determining from the digital data whether the at least one anomaly is present on the substrate.

33. The system of claim 32, wherein the array of resonant photonic open-feed antenna elements are supported on an optically transparent substrate.

34. The system of claim 33, wherein the optically transparent substrate is formed from material selected from the group consisting of $SiO_2$, BK7 and optical glass.

35. The system of claim 32, wherein the energy source is a laser having a characteristic wavelength between about 830 nm to about 400 nm.

36. The system of claim 32, wherein the open-feed antenna elements are bow-tie antenna elements.

37. The system of claim 32, wherein the open-feed antenna elements are closed flux path folded dipole antenna elements.

38. The system of claim 32, wherein the incident energy beam is directed toward the target substrate at an angle of $\theta$ degrees measured from the surface of the target substrate, such that at least two predominant orders of scattered radiation are created, comprising a forward scattered radiation order at an angle of 180-$\theta$ degrees measured from the surface of the target substrate containing the specular reflection of the incident energy beam, and a diffracted radiation order, containing scattered and re-radiated radiation from the target substrate and array of antenna elements.

39. The system of claim 38, wherein the filter is positioned to receive and filter only the diffracted radiation order and not the forward scattered radiation order.

40. The system of claim 39, wherein $\theta$ is 45 degrees.

41. The system of claim 32, wherein the processor has further functionality for determining from the digital data the location of the anomaly on the target substrate.

42. The system of claim 32, wherein the processor has further functionality for determining from the digital data whether the anomaly on the target substrate is a void or a particle.

43. The system of claim 32, wherein the processor has further functionality for determining from the digital data whether the anomaly on the target substrate is formed of metallic or non-metallic material.

44. A closed flux path resonant photonic open-feed folded dipole antenna element for concentrating the electromagnetic field strength of an incident electromagnetic wave having an characteristic wavelength ($\lambda$), comprising:

a dielectric substrate;

an outer conducting strip formed in a rectangular shape supported by the dielectric substrate, wherein the length of the rectangular shape is about $\lambda/2.8$ and the width of the rectangular shape is about $\lambda/4.8$, the outer conducting strip having a width of less than one-third of the width of the rectangular shape formed by the outer conducting strip, the outer conducting strip having a first and second length portion, the first and second length portions being parallel to one another and forming the length of the rectangular shape;

a first conducting strip, supported by the dielectric substrate, extending from the outer conducting strip toward the interior of the rectangular shape formed by the outer conducting strip, parallel to the first and second length portions and equidistant from the portions, the first conducting strip terminating in a first end; and a second conducting strip, supported by the dielectric substrate, extending parallel to the length portions and equidistant from the portions, the second conducting strip extending from a point on the outer conducting strip opposite the first conducting strip toward the interior of the rectangular configuration and terminating in a second end;

wherein the first and second ends are separated by a gap of about $\lambda/16$.

* * * * *